US008975222B2

(12) United States Patent
Lynch et al.

(10) Patent No.: US 8,975,222 B2
(45) Date of Patent: Mar. 10, 2015

(54) STABLE HIGH LIPID LIQUID FORMULA

(75) Inventors: Andrew Sean Lynch, Liverpool (GB); Simon Anders, Liverpool (GB); Paul Ronald, Liverpool (GB)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 13/701,794

(22) PCT Filed: Jun. 6, 2011

(86) PCT No.: PCT/NL2011/050396
§ 371 (c)(1),
(2), (4) Date: Feb. 28, 2013

(87) PCT Pub. No.: WO2011/152730
PCT Pub. Date: Dec. 8, 2011

(65) Prior Publication Data
US 2013/0157937 A1      Jun. 20, 2013

(30) Foreign Application Priority Data

Jun. 4, 2010   (WO) ................ PCT/NL2010/050343

(51) Int. Cl.
| A23L 1/29 | (2006.01) |
| A61K 38/00 | (2006.01) |
| A61K 9/107 | (2006.01) |
| A23L 1/30 | (2006.01) |
| A23L 1/305 | (2006.01) |
| A23L 1/308 | (2006.01) |
| A61K 31/20 | (2006.01) |
| A61K 31/733 | (2006.01) |
| A61K 36/48 | (2006.01) |
| A61K 38/01 | (2006.01) |
| A61K 38/17 | (2006.01) |

(52) U.S. Cl.
CPC ................ *A61K 9/107* (2013.01); *A23L 1/296* (2013.01); *A23L 1/3006* (2013.01); *A23L 1/3008* (2013.01); *A23L 1/3056* (2013.01); *A23L 1/308* (2013.01); *A23L 1/3081* (2013.01); *A61K 31/20* (2013.01); *A61K 31/733* (2013.01); *A61K 36/48* (2013.01); *A61K 38/018* (2013.01); *A61K 38/1709* (2013.01); *A23V 2002/00* (2013.01)
USPC .............................. 514/5.5; 530/360; 514/5.7

(58) Field of Classification Search
None
See application file for complete search history.

(56) References Cited

FOREIGN PATENT DOCUMENTS

| WO | WO-86/07262 A1 | 12/1986 |
| WO | WO-02/098242 A1 | 12/2002 |
| WO | WO-2009/072885 A1 | 6/2009 |
| WO | WO-2009/075573 A1 | 6/2009 |
| WO | WO-2009/099316 A1 | 8/2009 |
| WO | WO-2010/047581 A1 | 4/2010 |
| WO | WO-2010/047597 A1 | 4/2010 |

OTHER PUBLICATIONS

Coia et al, Shelf Life Study of Oil/Water Emulsions using Various Commercial Hydrocolloids, Journal of Food Science, 1987, 52, pp. 166-172.*
Protein, from www.hsph.harvard.edu/nutritionsource/What-should-you-eat/protein/, pp. 1-9, accessed Apr. 20, 2014.*
Lipids, from http://www2.chemistry.msu.edu/faculty/reusch/virt-txtjml/lipids.htm, pp. 1-10, accessed Apr. 20, 2014.*
Resistant starch, from www.precisionnutrition.com/all-about-resistant-starch, pp. 1-7, accessed Apr. 20, 2014.*
Soy fiber, from www.pacificsoy.com/soy_Fiber.html, pp. 1-2, accessed Apr. 20, 2014.*
Niness, Inulin and Oligofructose: What Are They?, J. Nutr., 1999, 129, pp. 1402S-1406S.*
Casein-*Homo sapiens*, from http://www.ncbi.nlm.nih.gov/protein/AAY68392.1, p. 1, accessed Apr. 20, 2014.*
Carbohydrates, from http://www2.chemistry.msu.edu/faculty/reusch/virttxtjml/carbhyd.htm, pp. 1-11, accessed Apr. 20, 2014.*
Sodium caseinate, from http://www.livestrong.com/article/495564-what-is-sodium-caseinate/, pp. 1-11, accessed Apr. 21, 2014.*
Glyceryl monostearate, from http://inrfood.com/ingredients/4281, pp. 1-4, accessed Apr. 21, 2014.*
International Search Report received in PCT/NL2011/050396 dated Dec. 13, 2011.
Anonymous "Nutricia stimulance multifibre mix module 400 gram", Mar. 20, 2008, XP-002624210.
Neal, Elizabeth G. et al., "The Ketogenic Diet for the Treatment of Childhood Epilepsy: A Randomised Controlled Trial," Lancet Neurology, Jun. 2008, vol. 7, pp. 500-506.
Prosky L, et al., "Determination of Insoluble, Soluble, and Total Dietary Fiber in Foods and Food Products: Interlaboratory Study," J. Assoc. Off. Anal. Chem., 1988, vol. 71, No. 5, pp. 1017-1023.
Titgemeyer, Evan C. et al., Fermentability of Various Fiber Sources by Human Fecal Bateria in Vitro 1-3, Am J Clin Nutr, 1991, vol. 53, pp. 1418-1424.

* cited by examiner

*Primary Examiner* — Julie Ha
*Assistant Examiner* — Li Ni Komatsu
(74) *Attorney, Agent, or Firm* — Gilberto M. Villacorta; Sunit Talapatra; Foley & Lardner LLP

(57) ABSTRACT

The present invention provides a ketogenic diet in the form of a sterile shelf stable ready to use formula, in particular a tube feed, comprising casein and dietary fiber.

10 Claims, No Drawings

STABLE HIGH LIPID LIQUID FORMULA

CROSS REFERENCE TO RELATED APPLICATIONS

The present application is a National Stage of International Application No. PCT/NL2011/050396 filed on Jun. 6, 2011, which claims the benefit of International Application No. PCT/NL2011/050343 filed on Jun. 4, 2010. The entire disclosures of which are incorporated herein by reference.

FIELD OF THE INVENTION

The present invention relates to liquid compositions comprising poorly soluble ingredients, such as proteins, lipids and nutritional fibres that can suitably be used in the manufacture of tube feeds, e.g for in patients in hospitals. Tube feeds are known in the art as being homogeneous liquid nutritional products which are administered to an individual via a tube. Ready to feed tube feeds are packed as a sterile liquid.

BACKGROUND OF THE INVENTION

Epilepsy is one of the most common neurological disorders after stroke, and affects at least 50 million people worldwide. It is diagnosed in a person having recurrent unprovoked seizures. These occur when cortical neurons fire excessively, hypersynchronously, or both, leading to temporary disruption of normal brain function. This might affect, for example, the muscles, the senses, consciousness, or a combination thereof. A seizure can be focal (confined to one part of the brain) or generalized (spread widely throughout the brain and leading to a loss of consciousness).

Epilepsy may occur for a variety of reasons; some forms have been classified into epileptic syndromes, most of which begin in childhood. Epilepsy is considered refractory to treatment when two or three anticonvulsant drugs have failed to control it. About 60% of patients will achieve control of their epilepsy with the first drug they use, whereas about 30% do not achieve control with drugs. When drugs fail, other options include epilepsy surgery, vagus nerve stimulation and the ketogenic diet. The ketogenic diet is often administered as a tube feed.

The ketogenic diet is effective in half of the patients who try it, and very effective in one third of the patients. In 2008, a randomised controlled trial showed a clear benefit for treating refractory epilepsy in children with the ketogenic diet, see Lancet Neurology 76: 500-506 (2008). There is some evidence that adults with epilepsy may benefit from the diet, and that a less strict regime, such as a modified Atkins diet, is similarly effective. The ketogenic diet has also been proposed as a treatment for a number of neurological conditions other than epilepsy; including patients experiencing epileptic syndromes, seizures and myoclonic jerk, persons in need of improvement of brain function or of cognitive skills, in particular of memory, for example patients suffering from Alzheimer's Disease or patients which suffer from a tumor, amyotrophic lateral sclerosis (ALS), Parkinson's disease, stroke, brain trauma, diabetes and obesity.

The ketogenic diet is a high-fat, adequate-protein, low-carbohydrate diet primarily used to treat difficult-to-control (refractory) epilepsy in children. The diet mimics aspects of starvation by forcing the body to burn fats rather than carbohydrates. Normally, the carbohydrates contained in food are converted into glucose, which is then transported around the body and is particularly important in fuelling brain function. However, if there is very little carbohydrate in the diet, the liver converts fat into fatty acids and ketone bodies. The ketone bodies pass into the brain and replace glucose as an energy source. An elevated level of ketone bodies in the blood, a state known as ketosis, leads to a reduction in the frequency of epileptic seizures.

Ketogenic formulas suitable for tube feeding should not form lumps or contain particles that form sediment, since this increases the risk of obstructing the tubes or restricting the flow. Also phase separation should be prevented, since one of the phases may remain in the package or tubing during feeding, which results in administration of an unbalanced nutrition and incomplete nutrition when the complete unit dose is not finished.

Thickeners are widely used in the art to prevent sedimentation of insoluble ingredients. However the viscosity of tube feeds is limited to a narrow range, in order to allow a constant and sufficiently high flow rate through the tubing when the diameter of the tube is small and a conventional administration pump is used. Especially for infants the tube feed diameter is relatively small thereby restricting the viscosity of the nutritional composition. Formulas that contain a high amount of fat are specifically sensitive to instability caused by phase separation. Similar considerations apply when the product is used as sip feed and a straw is used for consuming the product.

Presently many high-lipid food formulas are powder compositions that are prepared just before the administration of the tube feed. Ketocal Infant™ powder is an example of such a product. This has the advantage that the liquid product to be consumed by the patients does not need to be heated. Heating the product (e.g. sterilization) often results in sediment formation and phase separation. These physical processes are often aggravated during storage or cooling of the formula. The powder products have the disadvantage that the product is not ready to use, which is not convenient to the patients or nurses, and potential errors can be made in the preparation of the formula. In addition the use in tube feeding is limited due to instability issues of the formula. The stability of such products varies between 30 and 180 minutes depending on the batch of finished product tested. This is generally not stable enough for use in tube feed.

SUMMARY OF THE INVENTION

Different patient groups can potentially benefit from the administration of a liquid nutritional product comprising a lipid fraction that delivers at least 80% of the total calories of the composition. In the context of this document this is called a ketogenic diet.

The object of the present invention is to provide a shelf-stable liquid composition high in lipid. Phase separation and precipitation of the ingredients should be avoided. Shelf-stable is defined as having a stability of more than 6 months on the shelf under normal storage conditions, i.e. at an ambient temperature of between 18 and 25° C., and at a standard atmospheric pressure.

The inventors now surprisingly found that ready to use sterile liquid compositions comprising insoluble fibres and having such high fat content can be prepared by using a specific protein-fibre blend. This protein-fibre blend comprises a minimum amount of casein, e.g. one or more caseinates and specific dietary fibres. The dietary fibre fraction comprises at least two of resistant starch, soy fibre and inulin.

Both the selected fibres and casein were found to be able to stabilise an emulsion of the ketogenic diet. Without being bound by theory, the inventors hypothesise that the fibre, once hydrated will align itself into a large network. This gives structure to the liquid and retards coalescence and the flocculation of undissolved particles.

The composition according the invention can beneficially be used in the nutritional management of patients which are in need of a ketogenic diet. These patients include patients experiencing epileptic syndromes, seizures and myoclonic jerk, persons in need of improvement of brain function or of cognitive skills, in particular of memory, for example patients suffering from Alzheimer's Disease, patients which suffer from a tumor or amyotrophic lateral sclerosis (ALS), patients suffering from Parkinson's disease or stroke or brain trauma or, diabetes or obesity.

DETAILED DESCRIPTION OF THE INVENTION

The present invention thus concerns a sterile liquid composition comprising lipid that provides at least 80% of the total energy of the composition and that comprises at least 0.15 g casein per g lipid and that comprises at least two of resistant starch, soy fibre and inulin. Preferably the composition has a caloric density between 1 and 4 kcal/ml. Preferably the composition further comprises digestible carbohydrate.

In one embodiment, the present invention concerns a sterile liquid composition with a caloric density between 1 and 4 kcal/ml, comprising lipid, protein, digestible carbohydrates and dietary fibres, wherein the lipid provides at least 80% of the total calories of the composition and the protein comprises at least 0.15 g casein per g lipid, and wherein the dietary fibre comprises at least two selected from the group consisting of resistant starch, inulin and soy fibre.

The products according to the invention are homogeneous and have essentially no precipitation of particles that can potentially clog the tubing when administered as tube feed. Thus the liquid composition according to the invention provides in a convenient and accurate way proper amounts of the right nutrients.

The occurrence of constipation is a problem that is often present in neurological patients treated with a ketogenic diet. Advantageously it was found that the present composition improves the gastrointestinal problems which are often found to be associated with typical ketogenic diets. Thus the present composition also provides for the treatment and/or prevention of constipation in patients following a ketogenic diet.

In one embodiment the present invention concerns a sterile liquid composition with a caloric density between 1 and 4 kcal/ml, comprising lipid, protein, digestible carbohydrate and dietary fibre, wherein the lipid provides at least 80% of the total calories of the composition and the protein comprises between 1 and 8 g casein per 100 ml of liquid formula, and wherein the dietary fibre comprises at least two selected from the group consisting of resistant starch, inulin and soy fibre.

In one embodiment according to the invention, the dietary fibre in the sterile liquid composition comprises resistant starch, inulin and soy fibre.

In one embodiment according to the invention, the composition comprises at least 0.15 g casein per g lipid.

In a preferred embodiment the composition according to the present invention has a caloric density of at least 1.0 kcal/ml, preferably at least 1.3 kcal/ml, preferably at least 1.5 kcal/ml of composition. In another preferred embodiment of the present invention, the composition has an energy density of less than 4.0 kcal/ml, preferably less than 3.5 kcal/ml, preferably between 1.0 and 4.0 kcal/ml, preferably between 1.3 and 4.0 kcal/ml, preferably between 1.5 and 3.5 kcal/ml even more preferably between 1.4 and 2.5 kcal/ml, most preferred between 1.4 and 2.0 kcal/ml.

Casein

Without being bound by theory, the casein in the composition according to the present invention is likely to aid the formation of an emulsion. Once hydrated the large casein protein may align itself at the oil-water interface, with lipophilic amino acids or protein domains expected to reside in the oil phase and hydrophilic ones in the water phase. These hydrophilic domains are considered to be charged. This charge is considered to be important, as it is likely to help to repel other oil droplets coated with proteins by steric hindrance, and thus reduce the rate of coalescence. Proteins can also affect the viscosity of the liquid, if a large amount of protein and fat are used in an emulsion, the resulting emulsion will be of a higher viscosity. It has been found that not all proteins have these properties and/or are capable of preventing coalescence of the fat. Casein however has been found to be suitable for this purpose. The preferred casein source is selected from potassium and sodium caseinate. In particular sodium caseinate has been shown to provide excellent stability. Thus in one embodiment according to the present invention, the composition comprises sodium caseinate, or in other words, the casein is sodium caseinate. Preferably the composition according to the present invention comprises at least 1.5 g casein/100 ml. Other casein sources have the disadvantage that they are less heat stable and therefore not as effective as the sodium form in giving a stable emulsion in the liquid product. Since the liquid product is sterilized this is an important feature.

It implicitly follows from the requirement that the lipid provides at least 80% of the total energy of the composition, that the protein can maximally provide 20% of the total energy of the composition. Using the Atwater factors for calculating the contribution of calories of the macronutrients protein, digestible carbohydrate and fat, it follows that according to the invention the sterile liquid composition comprises less than 0.56 g protein per g lipid. Thus the sterile liquid composition according to the invention comprises less than 0.56 g casein per g lipid. In one embodiment, the sterile liquid composition according to the invention comprises less than 0.55 g protein per g lipid, preferably less than 0.54 g protein per g lipid. In one embodiment, the sterile liquid composition according to the invention comprises less than 0.55 g casein per g lipid, preferably less than 0.54 g casein per g lipid.

The amount of protein is preferably not too high to prevent that the composition has a too high viscosity making it unsuitable for tube feeding. A preferred amount of protein in the composition is therefore not higher than 8 g protein per 100 ml, preferably between 1 and 8 g/100 ml and even more preferably between 2 and 5 g/100 ml. Preferably the amount of casein in the composition according to the invention is not higher than 8 g casein per 100 ml, preferably between 1 and 8 g/100 ml and even more preferably between 2 and 5 g/100 ml. In one embodiment the present invention concerns a sterile liquid composition with a caloric density between 1 and 4 kcal/ml, comprising lipid, protein, digestible carbohydrate and dietary fibre, wherein the lipid provides at least 80% of the total calories of the composition and the protein comprises between 1 and 3 g casein per 100 ml of liquid formula, and wherein the dietary fibre comprises at least two selected from the group consisting of resistant starch, inulin and soy fibre. In one embodiment of the present invention, the viscosity of the liquid composition is lower than 500 mPa·s, measured at 20° C. (i.e. room temperature) at a shear rate of 100 $s^{-1}$, preferably between 10 and 200 mPa·s, more preferably between 10 and 100 mPa·s, most preferably below 50 mPa·s.

The viscosity may suitably be determined using a rotational viscosity meter using a cone/plate geometry. This viscosity is ideal for orally administering the liquid enteral nutritional composition according to the invention because a person may easily consume a serving having a low viscosity such as that displayed by the present invention. This viscosity is also ideal for unit dosages that are tube fed.

The pH is also important for the stability of the product. The inventors found that a pH between 6.5 and 7.6, preferably between 6.7 and 7.5 and even more preferably between 6.8 and 7.3 gives the most stable products without lumps and phase separation problems often seen in these high fat products.

Lipid

A lipid composition suitable for use in formulas according to the present invention preferably comprises as much as possible unsaturated fatty acids. Lipids comprising unsaturated fatty acids allow a much lower rate of phase separation and coalescence in the ready to use liquid product at temperatures between 3 and 29 degrees Celsius compared to lipids comprising mainly or consisting of saturated fatty acids. Therefore, in a preferred embodiment the lipid in the composition according to the invention comprises at least 65%, preferably at least 70%, even more preferably between 70 and 90%, most preferably between 75 and 85% unsaturated fatty acids based on total fatty acids present in the composition. Preferably the fatty acids comprise a large part of polyunsaturated fatty acids (PUFA) that have very advantageous dispersion characteristics. In a preferred embodiment the lipid in the composition according to the invention therefore comprises at least 15% PUFA, preferably between 15 and 35%, even more preferably between 20 and 30% based on the total fatty acid present in the composition.

In the context of this invention, lipid has its normal meaning in relation with nutritional compositions and thus refers to edible fat which is commonly provided as mono-, di-, and/or tri-acylglycerols and/or as free fatty acids. Preferably the lipid suitable for use in the sterile liquid composition according to the present invention comprises vegetable fat, preferably the lipid comprises rapeseed oil, corn oil and/or sunflower oil due to their readily availability, ease of formulation, absence of cholesterol and lower concentration of saturated fatty acids. Advantageously, in view of their benficial PUFA content, the lipid suitable for use in the sterile liquid composition according to the present invention preferably comprises algal oil and/or fish oil.

In one embodiment, the composition does not contain medium chain triglycerides (MCT).

Dietary fibres

Dietary fibres in combination with casein synergistically stabilize the high fat composition according to the invention. The inventors determined that when at least one dietary fibre selected from the group consisting of resistant starch, soy fibre and inulin fibres, is used in combination with casein a surprisingly stable product can be obtained.

The examples, see tables 1 and 2, show that when the resistant starch, e.g. NOVELOSE™, soy fibre, e.g. SOY FIBRE™ and inulin, e.g. BENEO™, are omitted from the final composition there is a significant effect on the overall homogeneity and therefore stability of the final product. The inventors further found that the stability of the product is severely affected when the amount of fibre is below 0.3 g/100 ml, resulting in phase separation. Therefore a preferred composition according to the present invention comprises at least one dietary fibre selected from the group consisting of resistant starch, soy fibre and inulin fibres, wherein said dietary fibre is preferably present in an amount between 0.3 and 5.0 g/100 ml, more preferably in an amount between 0.5 and 2.5 g/100 ml, and even more preferably in an amount between 0.7 and 1.5 g/100 ml of the composition.

Resistant starch, soy fibre and inulin are dietary fibres that are readily commercially available, e.g. from National Starch & Chemical, Fibred Group and Orafti repsectively.

Apart from the surprising effect of the dietary fibres on the stability of the liquid formula according to the present invention, dietary fibres have an important nutritional effect in patients treated with a ketogenic diet. Patients in need of the ketogenic diet experience gut problems which are typical to the exclusive consumption of very high amounts of lipids. The strict dietary regimen induces changes in gut flora by promoting growth of bacteria which tolerate and grow well on such diet. Normal diets which comprise nutritional fibres are frequently avoided, because they also comprise relatively a lot of digestible carbohydrates compared to the amounts of lipids and therefore destroy the effect of the ketogenic diets consumed at other moments. For an optimal effect on the intestinal gut function the inclusion of a mix of soluble and insoluble dietary fibres in the formula according to the present invention is preferred. Preferably these fibres can be selected from the group consisting of gum Arabic such as Acacia gum, wheat fibre such as Vitacel, pectin, cellulose or oligosaccharides thereof. Thus the composition according to the invention may also contain other dietary fibres than resistant starch, soy and inulin. Preferably other fibres are selected from the group consisting of gum Arabic such as Acacia gum, wheat fibre such as Vitacel, pectin, or oligosaccharides thereof.

Preferably the total amount of dietary fibre included in the liquid product is between 0.4 and 4 g/100 ml, preferably between 0.6 and 3.5, even more preferably between 0.8 and 3.0, and most preferably between 1.0 and 2.0 g/100 ml. Depending on the daily dose, this amount is sufficient to be effective in the treatment of constipation, and not too much for interfering with the stability of the product.

The term "fibre" or "dietary fibre" is used herein to denote plant-derived food material, in particular oligo- and polysaccharides (cellulose and hemicellulose), lignin, and resistant starch, that is not digested by the human (non-bacterial) enzymes of the intestinal tract. This means that fibre is that part of the food that is not absorbed in the small intestine and thus enters into the large intestine (colon).

The term "fermentable fibre" means fibre that undergoes (anaerobic) breakdown by microorganisms in the large intestine to smaller molecules, in particular to short-chain fatty acids, such as acetic, propionic and butyric acid. Fermentation also results in the production of gases, such as carbon dioxide, hydrogen and methane. Fibre fermentability may be determined e.g. by the method described in Amer. J. Clinical Nutrition (1991), 53, 1418-1424.

The term "soluble fibre" means that the fibre is at least 50% soluble according to the method described by L. Prosky et al., J. Assoc. Off. Anal. Chem. 71, 1017-1023 (1988).

Examples of soluble non-starch polysaccharides include inulin (a poly-saccharide mainly consisting of fructose units), pectin (a polysaccharide mainly consisting of galacturonic acid and rhamnose), beta-glucans (small cellulose-type branched glucose polymers), gum arabic, tragacanth, mucilages, guar and locust bean gum, agar, carageenans, alginates, xanthan and the like. Most of these soluble fibres are fermentable for the largest part. In particular the proportion of soluble non-starch polysaccharides is within the range of 20-40 wt. %.

Examples of insoluble non-starch polysaccharides include cellulose (for example derived from i.a. oat hull, soybeans, cereal bran) and hemicellulose (mostly branched arabinoxylans or galactans, e.g. from cereals, potatoes or soybeans) and lignin. Most of these insoluble fibres are partly fermentable or non-fermentable. In particular the proportion of insoluble non-starch polysaccharides is within the range of 20-40 wt. %.

Resistant starch is commonly known and generally consists of any type of starch that escapes digestion and intestinal absorption and can be formed during processing of starch containing foods. In some starches the crystalline structure will be altered or retrograded by these processes, which make the starch difficult to be digested. Resistant starch may also be obtained from raw foods, such as potatoes or green bananas. Resistant starch is normally insoluble and the fermentability varies with the source.

The inclusion of the fibre fraction normalizes the composition of the gut flora, in increasing the biosynthesis of acetic acid in the gut compared to that of propionic acid. This increases the acidity of the faeces. The improved gut flora also allows a better bioavailability of the lipid fraction of the product, which increases the ketogenic character of the product.

Emulsifier

In a preferred embodiment according to the invention the composition further comprises one or more, e.g. a blend of, emulsifiers to further improve stability and characteristics of the liquid composition.

Preferably the composition comprises one or more emulsifiers selected form the group consisting of propylene glycol alginate (Manucol Ester B) in a range between 0.001 and 0.1 g/100 ml, preferably between 0.005 and 0.05 g/100 ml, and even more preferably about 0.01 g/100 ml; citric acid esters of mono and diglycerides of fatty acids (Acidan; E472c) between 0.05 and 0.80 g/100 ml, preferably between 0.1 and 0.5 g/100 ml, even more preferred about 0.25 g/100 ml; glyceryl monostearate and glyceryl distearate (Dimodan; E471) in a range between 0.001 and 0.50 g/100 ml, preferably between 0.01 and 0.20 g/100 ml, even more preferably about 0.09 g/100 ml.

The inventors found that the combination of these emulsifiers was exceptionally helpful in creating a stable emulsion, thus in one embodiment the composition comprises propylene glycol alginate (Manucol Ester B) in a range between 0.001 and 0.1 g/100 ml, preferably between 0.005 and 0.05 g/100 ml, and even more preferably about 0.01 g/100 ml; and citric acid esters of mono and diglycerides of fatty acids (Acidan) between 0.05 and 0.80 g/100 ml, preferably between 0.1 and 0.5 g/100 ml, even more preferred about 0.25 g/100 ml; and glyceryl monostearate and glyceryl distearate (Dimodan) in a range between 0.001 and 0.50 g/100 ml, preferably between 0.01 and 0.20 g/100 ml, even more preferably about 0.09 g/100 ml. The use of these emulsifiers improved the stability of the final composition and are therefore preferably present in a composition according to the present invention.

Combination of Casein and Dietary Fibre

In the examples, see table 3, the results of a stability study are detailed. In this study varying amounts of lipid with or without different protein sources and with or without different dietary fibres were investigated.

The inventors discovered a relationship between the amount of casein+fibres and the amount of lipid that results in stable compositions. The weight ratio (casein+fibre): lipid is preferably between 0.09 and 0.80, preferably between 0.12 and 0.40, even more preferably between 0.15 and 0.35 and most preferably between 0.20 and 0.30.

It was found that the combination of all three fibres resistant starch, soy fibre and inulin with sodium caseinate gave the most stable composition. Therefore, a preferred composition according to the present invention comprises sodium caseinate, resistant starch, soy fibre and inulin.

Dosage Unit

The liquid composition according to the invention may have the form of a complete food, i.e. it can meet all nutritional needs of the user. As such, it preferably contains 1200 to 2500 kcal per daily dosage depending on the age of the user. The complete food can be in the form of multiple dosage units, e.g. from 4 (250 ml/unit) to 20 (50 ml/unit) per day for an energy supply of 1500 kcal/day using a liquid enteral nutritional composition according to the invention of 1.5 kcal/ml.

Preferably the composition according to the present invention is used as a tube feed. The improved stability of the ready to use liquid composition makes the product specifically suitable for use as tube feed.

The composition according to the present invention is particularly suitable to be used by or administered to infants or children between 1 and 10 years of age.

For infants between 1-3 years the preferred daily dose of the composition according to the present invention provides between 1000 and 1500 kcal/day, for infants between 4-6 years of age this is between 1500 and 1800 kcal/day and for 7-10 years this is between 1800 and 2000 kcal/day. For these infants the composition according to the present invention is designed to be used as sole nutrition. For older children the composition according to the present invention may be used as supplement, for example to be used in addition to a non-medical food. Preferably as a supplement, the liquid enteral nutritional composition contains per daily dosage less than 1500 kcal, in particular as a supplement, the liquid enteral nutritional composition contains 400 to 1000 kcal per daily dose. The food supplement can be in the form of multiple dosage units, e.g. from 2 (250 ml/unit) to 10 (50 ml/unit) per day for an energy supply of 1000 kcal/day using a liquid enteral nutritional composition according to the invention of 2.0 kcal/ml.

In one embodiment of the present invention, a unit dosage comprises any amount of the liquid composition according to the invention between 10 ml and 250 ml, the end values of this range included, preferably any amount between 25 ml and 200 ml, the end values of this range included, more preferably any amount between 50 ml and 150 ml, the end values of this range included, most preferably about 125 ml.

For example, a person receiving 50 ml unit dosages can be given 10 unit dosages per day to provide nutritional support using a liquid enteral nutritional composition according to the invention of 2.0 kcal/ml. Alternatively a person receiving 125 ml unit dosages can be given 4 or 5 or 6 or 7 or 8 unit dosages per day to provide nutritional support using a liquid enteral nutritional composition according to the invention of 2.0 kcal/ml. Such small dosage units are preferred because of better compliance.

In one embodiment of the present invention, the composition according to the invention is packaged. The packaging may have any suitable form, for example a block-shaped carton, e.g. to be emptied with a straw, a carton or plastic beaker with removable cover, a small-sized bottle for example for the 80 ml to 200 ml range, and small cups for example for the 10 ml to 30 ml range.

Method for Preparing Compositions According to the Present Invention

The composition according to the present invention can be prepared using standard technology comprising the steps of a) mixing the ingredients, b) pre-heating the mixed ingredients of step a), c) sterilisation using heat treatment, d) homogenisation, e) cooling and f) packaging. Depending on the exact composition of the product, the specific circumstances of the different steps may need to be adapted using routine optimalisation steps.

Application

The invention also concerns a method for the nutritional management of patients which are in need of a ketogenic diet, said method comprising administering a sterile liquid composition according to the present invention.

In other words, the invention concerns the use of a sterile liquid composition as defined herein, for the preparation of a nutritional composition for the nutritional management of patients which are in need of a ketogenic diet The invention can also be worded as a sterile liquid composition as defined herein for use in the nutritional management of patients which are in need of a ketogenic diet.

In one embodiment, the patients which are in need of a ketogenic diet are patients experiencing epileptic syndromes, seizures and myoclonic jerk, persons in need of improvement of brain function or of cognitive skills, patients suffering from Alzheimer's Disease, patients which suffer from a tumor or from amyotrophic lateral sclerosis.

The invention also concerns a method for the prevention of epileptic seizures or the treatment of one or more selected from the group consisting of epilepsy, gut motility disorders including constipation, patients suffering from Alzheimer's Disease, and patients suffering from a tumor, said method comprising administering a sterile liquid composition according to the present invention.

The invention can also be worded as the use of a composition comprising lipid, casein and at least one selected from the group consisting of resistant starch, inulin and soy fibre for the manufacture of a sterile liquid composition with a caloric density between 1 and 4 kcal/ml, wherein the lipid provides at least 80% of the total calories of the composition for the prevention of epileptic seizures or the treatment of epilepsy, gut motility disorders including constipation, patients suffering from Alzheimer's Disease, and patients suffering from a tumor.

The invention can also be worded as a sterile liquid composition as defined herein for use in the prevention of epileptic seizures or treatment of epilepsy, gut motility disorders including constipation, patients suffering from Alzheimer's Disease, and patients suffering from a tumor.

The compostions according to the present invention are particularly suitable for the treatment and prevention of refractory epilepsy in children between 1 and 10 years of age.

EXAMPLES

Example 1

Preferred Composition According to the Invention

| COMPONENT | UNIT | Per 100 ml |
|---|---|---|
| Energy | kJ | 620 |
|  | kcal | 150 |
| Protein/Protein | g | 3.09 |
| whey |  | 0.79 |
| casein |  | 2.30 |
| Carbohydrate | g | 0.61 |
| of which sugars | g | 0.39 |
| Fat | g | 14.8 |

-continued

| COMPONENT | UNIT | Per 100 ml |
|---|---|---|
| Saturates | g | 2.4 |
| Monounsaturates | g | 8.6 |
| Polyunsaturates | g | 3.8 |
| Fibre, dietary | g | 1.12 |
| SOY FIBRE ™ | 0.35 |  |
| VITACEL ™ | 0.14 |  |
| RAFTILOSE ™ | 0.12 |  |
| BENEO ST ™ | 0.25 |  |
| NOVELOSE ™ | 0.1 |  |
| *Acacia* Gum | 0.16 |  |
| 1. Protein/Protein | En %* | 8.2 |
| 2. Carbohydrates | En %* | 1.6 |
| 3. Fat | En %* | 88.7 |
| 4. Fibre | En %* | 1.5 |
| Total | En % | 100 |

*The Atwater constants 9 and 4 kcal/g dry weight are used for calculating the energy content of lipids and protein or digestible carbohydrates respectively. For nutritional fibre the energy density of 2 kcal per g dry weight is applied.

Example 2

Rheological Assessment of Different Dietary Fibres

In order to determine the stability of the emulsion, the samples were examined using an amplitude sweep oscillation.

An amplitude sweep involves rotations at different amplitudes but at a constant frequency and temperature. They are usually done to determine the G', G" cross over and the length of the linear viseoelastic range, which provides an insight into the structure of a liquid and therefore can be used to predict storage stability. To perform an amplitude sweep the liquid is exposed to larger amounts of strain from 0.1 to 100% strain, this strain relates to the amplitude of deformation, i.e. the cone rotates back and forth for a greater distances for larger amplitudes. At 100% strain the distance of the oscillation is the same as the gap between the cone and the plate, at the edge of the cone the distance travelled is the greatest, at the centre there is no gap and the distance travelled is 0. As the cone moves forward and backwards with greater amounts of strain, more energy is put into the liquid, the amount of energy that the liquid gives back in the reformation is measured.

The experiments were performed on an Anton Paar MCR301 rheometer with a plate and 75 mm cone 1° pitch angle. The measurements were done at 25° C., at 1 Hz oscillation frequency and a sweep 0.1-100% strain resulting in 5 data points per decade amplitude ramp. All measurements were done according to the instructions of the manufacturer.

The storage modulus G' measures the amount of deformation energy that is stored when the liquid has been under strain. Once the strain is removed from the liquid, this stored deformation energy is used to help the reformation process, e.g. like a spring that has been under load, once the load has been removed the energy stored in the spring is what drives it back.

The loss modulus G" is the deformation energy that is used by the sample once under strain. Once the strain is removed, it is not available to help with the reformation process and is lost.

An ideal viscous liquid does not have any storage modulus as all the energy is lost in the deformation, and therefore has a high loss modulus.

An ideal solid, does not lose any energy in the deformation process and therefore all the energy is available for reformation and it has a high storage modulus.

The tested liquids are visco-elastic liquids they exhibit both storage (viscous) and loss (solid) modulus.

For a liquid that is placed under increasing strain, there is a critical point in which the storage modulus drops below the loss modulus. This point is known as cross over point and is at the end of the linear viscoelastic range (LVR). The more strain the liquid can accommodate before this cross over, the more the liquid has an internal structure and therefore the more stable the product is.

The length of the LVR, cross over and distance between the G' and G" curves in the LVR are only indicators of structural strength of the internal network of the liquid. A dispersion/emulsion that has high structural strength on the rheometer may still exhibit fluid loss/partial drop for several factors, for example due to the weight and amount of un-dissolved particles, syneresis/retrogradation of gels, coalescence of fats and so on, which can overpower the internal network of a liquid.

Along with the cross over point several other rheological properties were screened during this study. A breakdown of these terms can be found below and the resulting test data given in Table 1.

TABLE 1

Rheological Properties

| Sample ID | Raw material omitted | $\tau_{crit}$ (Pa) | $G^*$ at $\tau_{crit}$ (Pa) | $\tan(\delta)$ at $\tau_{crit}$ (Pa) | G' G" cross over (% Strain) |
|---|---|---|---|---|---|
| 2842-A | Soy fibre | 0.00276 | 0.422 | 0.726 | 2.66 |
| 2842-B | NOVELOSE ™ | 0.104 | 2.55 | 0.455 | 10.88 |
| 2842-C | BENEO ST ™ | 0.0188 | 1.67 | 0.457 | 7.295 |
| 2842-D | *Acacia* gum | 0.0768 | 8.78 | 0.366 | 46.55 |
| 2842-E | VITACEL ™ | 0.0297 | 1.18 | 0.454 | 26.8 |
| 2842-F | RAFTILOSE ™ | 0.0145 | 2.45 | 0.418 | 4.08 |

From the particle size distribution in table 1, and the rheological and visual assessment data in table 2 it can be shown that when the NOVELOSE™, SOY FIBRE™ and BENEO™ are omitted from the final product formulation there is a significant effect on the overall homogeneity and therefore stability of the final product.

It is therefore concluded that resistant starch, soy fibre and Inulin are contributing the most to the desired effects and are expected to perform the best in the stability tests of the complete ketogenic formulas.

In addition the inclusion of the fibre increases transit time of the food through the gut and increases gut motility, probably because of an effect on the endocrine and nervous systems in the gut.

Caseinates include various salts (Na, K, Ca, Mg or mixtures thereof), isolated from dairy products in various ways, and may include at least a beta casein from bovine milk.

Example 3

Rheological Properties and Visual Assessment

This study looked at the effect that varying the selected fibres from example 2 in combination with different levels and types of other functional ingredients has on the product stability. This stability was again assessed in terms of the rheological cross over point and also visual assessment.

In Table 2 the results of this study are detailed. In this study varying amounts of lipid with or without different protein sources and with or without different dietary fibres were investigated.

As can be seen from the data, the most stable product in terms of cross over and separation are samples that were produced using all three of the fibres selected from the screening design study and that have a caseinate protein source present.

Samples 100404 and 100412 contained all of the selected fibres and a casein protein source and gave the highest cross over points. Sample 100412 however contained both casein and soy fibre, without significantly increasing the cross over point when compared to 100404, which would indicate that significantly increasing the protein casein content and introducing a high level of soy protein isolate does not improve the cross over point. Additionally the presence of a large amount of protein resulted in the product having an increased viscosity making it unsuitable for tube feeding.

The requirement for the protein source to be casein is also demonstrated by samples 100410 and 100405, which both contained all 3 fibres but contained soy protein at differing levels but no casein or caseinate. Sample 100405 also has a significantly higher fat content when compared to sample 100410 but with no improved formulation stability as shown by the low cross over point and poor visual stability.

TABLE 2

Rheology and Visual Assessment per 30 kg batch

| Sample no | Fat Content (g) | Na Caseinate (g) | Soy Protein Isolate (g) | NOVELOSE (g) | SOY FIBRE (g) | BENEO (g) | Cross over % strain | separation 24 hr hang |
|---|---|---|---|---|---|---|---|---|
| 100404 | 4292 | 795 | 0 | 90 | 140.7 | 85.2 | 45.09 | None |
| 100412 | 6438 | 1193 | 1193 | 90 | 140.7 | 85.2 | 43.28 | None |
| 100406 | 2146 | 1193 | 0 | 90 | 0 | 85.2 | 16.55 | None |
| 100409 | 6438 | 0 | 1193 | 90 | 0 | 0 | 11.31 | Total |
| 100407 | 6438 | 1193 | 0 | 0 | 140.7 | 0 | 9.683 | None |
| 100411 | 4292 | 596.4 | 596.4 | 0 | 0 | 0 | 7.6 | Total |
| 100410 | 2146 | 0 | 1193 | 0 | 140 | 85.2 | 7.071 | Total |
| 100413 | 6438 | 0 | 0 | 0 | 0 | 85.2 | 6.67 | Total |
| 100405 | 4329 | 0 | 795 | 90 | 140.7 | 85.2 | 6.102 | Total |
| 100408 | 2146 | 0 | 0 | 90 | 140.7 | 0 | 5.52 | Total |
| 100414 | 2146 | 1193 | 1193 | 0 | 0 | 0 | 3.56 | Total |

The advantage of the presence of the three dietary fibres in combination with the casein protein source is shown by samples 100414, 100411 and 100406. These samples contained the casein source, but are missing some or all of the three fibres and all showed low cross over values and had extensive visual separation.

Samples that contained soy protein or no protein, and had one or more of the three dietary fibres removed, showed low cross over values and exhibited visual separation on standing.

Particle size was measured using a Malvern S laser particle diffraction analyser, using a liquid measuring cell according to the instructions of the manufacturer.

The invention claimed is:

1. A sterile liquid composition having a caloric density between 1 and 4 kcal/ml, comprising lipid, protein, carbohydrates and dietary fibers, wherein:
   (a) the lipid provides at least 80% of the total calories of the composition and comprises between 65 and 90% of unsaturated fatty acids on total fatty acids,
   (b) the protein comprises at least 0.15 and 0.56 g casein per g lipid of the composition, and
   (c) the dietary fiber comprises at least two selected from the group consisting of resistant starch, inulin and soy fiber in an amount of at least 0.3 and 5.0 g per 100 ml of the composition.

2. The sterile liquid composition according to claim 1, having a pH between 6.5 and 7.6.

3. The sterile liquid composition according to claim 1, wherein the protein comprises between 1 and 3 g casein per 100 ml.

4. The sterile liquid composition according to claim 1, wherein the dietary fiber comprises resistant starch, inulin and soy fiber.

5. The sterile liquid composition according to claim 1, wherein the casein is sodium caseinate.

6. The sterile liquid composition according to claim 1, wherein the caloric density is between 1.4 and 2.0 kcal/ml.

7. The sterile liquid composition according to claim 1, wherein the lipid comprises at least 70% unsaturated fatty acids based on total fatty acids present in the composition.

8. The sterile liquid composition according to claim 1, wherein the composition further comprises one or more selected from:
   (i) 0.001-0.1 g/100 ml propylene glycol alginate,
   (ii) 0.05-0.80 g/100 ml citric acid esters of mono and diglycerides of fatty acids, and
   (iii) 0.001 and 0.50 g/100 ml glyceryl monostearate and glyceryl distearate.

9. The sterile liquid composition according to claim 1, having a weight ratio (casein+fiber): lipid between 0.12 and 0.40.

10. A method for the nutritional management of patients having conditions selected from the group consisting of epileptic syndromes, seizures, myoclonic jerk, Alzheimer's Disease, tumor, amyotrophic lateral sclerosis, Parkinson's disease, stroke, brain trauma, diabetes and obesity, the method comprising administering to the patients an effective amount of a sterile liquid composition having a caloric density between 1 and 4 kcal/ml, comprising lipid, protein, carbohydrates and dietary fibers, wherein:
   (a) the lipid provides at least 80% of the total calories of the composition and comprises between 65 and 90% of unsaturated fatty acids on total fatty acids,
   (b) the protein comprises between 0.15 and 0.56 g casein per g lipid of the composition, and
   (c) the dietary fiber comprises at least two selected from the group consisting of resistant starch, inulin and soy fiber in an amount between 0.3 and 5.0 g per 100 ml of the composition.

* * * * *